(12) United States Patent
Hosokawa et al.

(10) Patent No.: US 6,210,687 B1
(45) Date of Patent: Apr. 3, 2001

(54) FAT EMULSION CONTAINING XANTHINE DERIVATIVE

(75) Inventors: Toshihito Hosokawa; Kenji Iwata; Yuji Kawaguchi; Yasuki Kato; Kunio Ito, all of Shizuoka-ken (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/230,984

(22) PCT Filed: Aug. 7, 1997

(86) PCT No.: PCT/JP97/02773

§ 371 Date: Mar. 24, 1999

§ 102(e) Date: Mar. 24, 1999

(87) PCT Pub. No.: WO98/05334

PCT Pub. Date: Feb. 12, 1998

(30) Foreign Application Priority Data

Aug. 7, 1996 (JP) .................................................. 8-224399

(51) Int. Cl.⁷ .......................... A61K 9/107; A61K 99/127
(52) U.S. Cl. .......................... 424/400; 424/450; 514/257; 514/213; 514/267; 514/938
(58) Field of Search ................................. 424/400, 450; 514/257, 263, 267, 937–943

(56) References Cited

U.S. PATENT DOCUMENTS 4,146,621 * 3/1979 Voorhees .............................. 424/240

FOREIGN PATENT DOCUMENTS

| 63-48223 | 2/1988 | (JP) . |
| 5-59056 | 3/1993 | (JP) . |
| 94/16702 | 4/1994 | (WO) . |

* cited by examiner

Primary Examiner—Gollamudi S. Kishore
(74) Attorney, Agent, or Firm—Fitzpatrick, Cella, Harper & Scinto

(57) ABSTRACT

An oil-in-water emulsion containing a xanthine derivative represented by

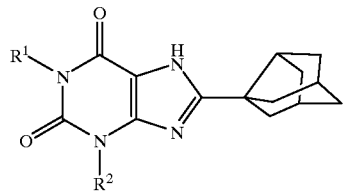

or its pharmacologically acceptable salt, wherein the xanthine derivative or salt is present within an oil phase of the emulsion.

59 Claims, No Drawings

FAT EMULSION CONTAINING XANTHINE DERIVATIVE

This application is a 371 of PCT/JP97/02773 filed Aug. 7, 1997.

TECHNICAL FIELD

The present invention relates to a fat emulsion containing a xanthine derivative or a pharmacologically acceptable salt thereof, which exhibits an adenosine A1 receptor antagonizing activity, and which has antihypertensive activity, diuretic activity, kidney-protecting activity, bronchiodilatary activity, brain function-improving activity and antidemential activity.

TECHNICAL BACKGROUND

Renal insufficiency, especially, acute renal insufficiency is such a serious disease that waste materials are accumulated in the blood owing to the deficiency of the renal function, and the development of an agent for preventing, curing or treating the renal insufficiency has been in demand. It is required to elucidate the renal function and to develope an appropriate treatment of the renal functional insufficiency.

It has been long known that xanthines such as caffeine, theophylline and the like possess diuretic activity. In recent years, studies have been made with respect to the diuretic activity of these xanthines, and it has been clarified that the xanthines act as an antagonist of an adenosine receptor. Further, in recent years, it has been discovered that 8-(3-noradamantyl)-1,3-dipropylxanthine (hereinafter sometimes referred to as "KW-3902") exhibits an excellent adenosine receptor antagonizing activity, and this compound has been developed as a medicine having an antihypertensive activity, a diuretic activity and kidney-protecting activity (F. Suzuki et al., J. Med. Chem., 35, 3066 (1992)). KW-3902 has attracted attention as a medicine which is especially effective for treating acute renal insufficiency. This KW-3902 is deemed effective in the parenteral administration. KW-3902 is sparingly soluble in water, and it is difficult to produce its preparations. In addition, the compound is problematic in a long-term storage stability. Thus, the development thereof as a medicine has posed a serious problem.

Meanwhile, a fat emulsion (lipid microsphere) has been already clinically applied for feeding, and also studies to apply the fat emulsion to preparation of an antiinflammatory antalgic agent have been conducted (Mizushima et al., "SAISHIN IGAKU", vol. 40, No. 9, pp. 1806–1813, 1985). However, medical ingredients which can be formulated with a fat emulsions are limited, and there have been problems that the stability thereof or the absorption of active ingredients varies depending on the ingredients, the amount, the physical form and the like of the fat emulsion.

DISCLOSURE OF THE INVENTION

The present inventors have conducted studies on production of pharmaceutical preparations of xanthine derivatives, especially 8-(polycycloalkyl)xanthines having excellent long-term storage stability, and have consequently found that pharmaceutical preparations which have high content of sparingly-soluble xanthine derivatives, which exhibit excellent long-term storage stability and which are especially suitable for parenteral administration are obtained through formulation using a fat emulsion.

The present invention is to provide a stable pharmaceutical preparation of a xanthine derivative or its pharmacologically acceptable salt suitable for parenteral administration. More specifically, the present invention is to provide a pharmaceutical preparation which contains a large amount of a xanthine derivative or its pharmacologically acceptable salt having antihypertensive activity, diuretic activity and kidney-protecting activity, which is especially useful as an agent for preventing, curing or treating renal insufficiency and which has excellent long-term storage stability. That is, the present invention is to provide a stable fat emulsion containing a 8-(polycycloalkyl)xanthine or its pharmacological acceptable salt.

The present invention relates to a fat emulsion containing a large amount of a xanthine derivative [hereinafter referred to as "Compound (I)"] represented by formula (I)

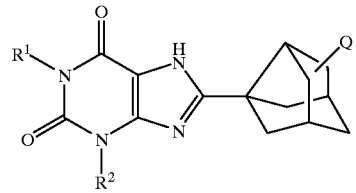

(I)

wherein $R^1$ and $R^2$ are the same or different and each represents a substituted or unsubstituted lower alkyl group, and Q represents hydrogen, a hydroxyl group or a hydroxyl group derivative or its pharmacologically acceptable salt, and having an excellent long-term storage stability.

In the definition of formula (I), the lower alkyl group includes linear or branched lower alkyl groups having from 1 to 8 carbon atoms, preferably from 1 to 6 carbon atoms, more preferably from 1 to 3 carbon atoms, such as methyl, ethyl, propyl, n-propyl, isopropyl, n-butyl, isobutyl, sec-butyl, tert-butyl, pentyl, neopentyl and hexyl. Preferable are methyl, ethyl and n-propyl. Examples of the substituent of the substituted lower alkyl group include a hydroxyl, acyl group such as an acetyl group, a carbonyl group (O=) and lower alkoxy group. Of these substituents, a hydroxyl group and an acetyl group are preferable. The lower alkyl group of the lower alkoxy group means the same groups as mentioned above for the lower alkyl group.

Examples of the hydroxyl group derivative of the substituent Q include an acyloxy group such as an acetoxy group and a lower alkoxy group such as a methoxy group.

Examples of the pharmacologically acceptable salt of Compound (I) include an acid addition salt, a metal salt, an ammonium salt, an organic acid amine addition salt and an amino acid addition salt which are pharmacologically acceptable.

Examples of the pharmacologically acceptable acid addition salt of Compound (I) include inorganic acid salts such as a hydrochloride, a sulfate and a phosphate; and organic acid salts such as an acetate, a maleate, a fumarate, a tartrate and a citrate. Examples of the pharmacologically acceptable metal salt include alkali metal salts such as a lithium salt, a sodium salt and a potassium salt; alkaline earth metal salts such as a magnesium salt and a calcium salt; an aluminum salt; and a zinc salt. Examples of the pharmacologically acceptable ammonium salt include salts of ammonium and tetramethylammonium. Examples of the pharmacologically acceptable organic amine addition salt include addition salts of morpholine and piperidine. Examples of the pharmacologically acceptable amino acid addition salt include addition salts of lysine, glycine, phenylalanine, glutamic acid and aspartic acid.

Compound (I) or its pharmacologically acceptable salt can be produced by various methods, for example, by the method described in Japanese Laid-Open (Kokai) No. 173,889/1991.

Specific examples of Compound (I) are shown in Table 1.

TABLE 1

| Compound Number | $R^1$ | $R^2$ | X |
|---|---|---|---|
| 1 | n-$C_3H_7$ | n-$C_3H_7$ | (structure) |
| 2 | n-$C_3H_7$ | n-$C_3H_7$ | (structure)—OH |
| 3 | n-$C_3H_7$ | n-$C_3H_7$ | (structure)—OH, OH |
| 4 | $CH_3CHCH_2$ \| OH | n-$C_3H_7$ | (structure)—OH |
| 5 | $CH_3CCH_2$ ‖ O | n-$C_3H_7$ | (structure)—OH |

Compound No. 1 in the above Table 1 is 8-(3-noradamantyl)-1,3-dipropylxanthine (KW-3902).

The fat emulsion of the present invention contains Compound (I) represented by the formula (I) as an active ingredient, a fatty oil, a surfactant and a pharmaceutically acceptable carrier.

More specifically, the fat emulsion of the present invention contains the fatty oil in an amount of from 0.5 to 30% (w/v) of fat emulsion, the surfactant in an amount of from 0.1 to 2 times by weight based on the fatty oil, and the pharmaceutically acceptable carrier.

With respect to the fat emulsion of the present invention, the particle diameter is between 0.005 and 0.3 μm, preferably between 0.02 and 0.15 μm.

The fat component used in the fat emulsion of the present invention is not particularly limited so long as it is parenterally administrable. Preferable examples thereof include vegetable oils such as soybean oil, sesame oil, olive oil and coconut oil. More preferable is soybean oil.

With respect to the surfactant to be used in the fat emulsion of the present invention, any surfactant can be used so long as an O/W emulsion can be formed, and the surfactant can be administered parenterally. Preferable examples thereof include egg yoke lecithin, soybean lecithin, highly purified phosphatidyl choline, phosphatidyl ethanolamine, phosphatidyl glycerol, phosphatidic acid, lysolecithin, polyoxyethylenesorbitan fatty acid ester, polyoxyethylene fatty acid ester, polyoxyethylated hydrogenated castor oil derivative, polyoxyethylene higher alcohol, and polyoxypropylene polyoxyethylene alkyl ether. More preferable is highly purified phosphatidyl choline.

With respect to the ratios of the ingredients of the fat emulsion in the present invention, as noted above, the amount of the fat component is between 0.5 and 30% (w/v) based on the total amount of the fat emulsion, and that of the surfactant is between 0.1 and 2 times (weight ratio) of the above-mentioned fat component. An appropriate amount of water is contained in the emulsion.

The fat emulsion can contain, in addition to the above-mentioned ingredients, an emulsification aid, a stabilizer, an isotonic agent, an antiseptic and the like as required. In the present invention, a fat emulsion containing, besides the fat component and the surfactant, an emulsification aid and an isotonic agent is preferable.

As the emulsification aid as used in the fat emulsion of the present invention, a saturated or unsaturated fatty acid having from 6 to 22 carbon atoms, preferably from 12 to 20 carbon atoms, or its pharmaceutically acceptable salt is preferable. Examples thereof include lauric acid, myristic acid, palmitic acid, stearic acid and oleic acid. More preferable is oleic acid. The amount of the emulsification aid is 3% (w/v) or less, preferably up to 1% (w/v) based on the total amount of the fat emulsion.

Examples of the isotonic agent used in the fat emulsion of the present invention include glycerin and dextrose. Preferable is glycerin.

Preferable examples of the stabilizer used in the fat emulsion of the present invention include cholesterols and phosphatidic acid. The amount thereof is preferably up to 5% (w/v). Preferable examples of the antiseptic used in the fat emulsion of the present invention include benzoic acid and parabens.

Further, the fat emulsion of the present invention can also be used as a freeze-dried preparation. At this time, an excipient to be used can further be added thereto. Examples of the excipient include mannitol, lactose, maltose, sucrose and inositol.

The amount of Compound (I) as the active ingredient of the fat emulsion in the present invention can properly be controlled depending on the form of the fat emulsion. Generally, it is between 0.01 μg/ml and 10 mg/ml, preferably between 0.1 μg/ml and 5 mg/ml, more preferably between 0.1 μg/ml and 3 mg/ml of the fat emulsion. It is one of the characteristics of the present invention that sparingly soluble Compound (I) can be contained in a large amount.

The fat emulsion of the present invention can be produced, for example, by the following method.

That is, the fat component, the surfactant, Compound (I) and optionally the emulsification aid and the stabilizer in predetermined amounts are mixed, and heated as required to form a solution. The solution is homogenized using an ordinary homogenizer (for example, a homomixer). Subsequently, water containing necessary amounts of the isotonic agent, the stabilizer and the like is added thereto as required, and the mixture is coarsely emulsified using a homogenizer to obtain an oil-in-water emulsion. Then, the resulting suspension is emulsified again by using homogenizer (for example, a high-pressure emulsifier such as MANTON-GAULIN HOMOGENIZER) until a droplet particle diameter becomes between 0.005 and 0.3 μm. From the standpoint of the production, additives such as a stabilizer, an isotonic agent, an antiseptic and the like may be added after the formation of the fat emulsion.

The product can be purified through dialysis or gel filtration as required.

The fat emulsion of the present invention can be sterilized and dispensed into an ampoule and then it can be sealed. Further, it can also be freeze-dried as required to form a freeze-dried preparation. The freeze-dried preparation can be used as an emulsion upon using an appropriate solvent when in use.

The fat emulsion of the present invention can be administered in various manners. Parenteral administration is preferable. The parenteral administration includes intravenous, intramuscular and subcutaneous administrations. The fat emulsion of the present invention is preferably used as an injection. However, it is not critical.

The present invention provides a pharmaceutically useful fat emulsion which contains a large amount of Compound (I), especially 8-(3-noradamantyl)-1,3-dipropylxanthine and which exhibits an excellent long-term storage stability.

EXAMPLE

The present invention is illustrated specifically by referring to the following Examples. However, the present invention is not limited thereto.

Five-hundred milligrams of KW-3902 (Compound No. 1 in Table 1,; KW-3902 is referred to hereinafter), 50 g of a soybean oil and 2.4 g of oleic acid were heat-mixed at approximately 60° C. Fifty grams of highly purified phosphatidyl choline, 22.1 g of glycerin and water for injection were added thereto to adjust the total amount to 1,000 ml. The mixture was stirred using a homomixer to form a coarse emulsion. The pH of the coarse emulsion was adjusted to 7, and subjected to emulsification at a high pressure using a microfluidizer to obtain a fine fat emulsion. The emulsion was cooled to room temperature, filtered using a membrane filter having a pore diameter of 0.2 μm, and poured into glass containers. The glass containers were purged with a nitrogen gas, and closed.

Test Example

The KW-3902-containing fat emulsions prepared in Example were stored at 25° C. and 40° C. in a thermostat for 30 days, and the residual amount of KW-3902, the discoloration of the fat emulsion and the average particle diameter thereof were measured. The residual amount of KW-3902 was measured through high-performance liquid chromatography under the following conditions. The discoloration was evaluated by diluting to 10 times with isopropyl alcohol and dissolving the fat emulsion and then measuring the absorbance at a wavelength of 455 nm. The average particle diameter was measured using a dynamic light scattering photometer DLS-700 (Otsuka Denshi). The results are shown in Table 2.

High-performance liquid chromatography analysis conditions:

Column: Shim-pack CLC-ODS

Mobile phase: acetonitrile: 20 mM potassium dihydrogen phosphate mixed solution (65:35)

Flow rate: 1.0 ml/min

Detection wavelength: Ultraviolet absorption photometer (280 nm)

TABLE 2

Stability of a KW-3902-containing fat emulsion

| Sample | Immediately after formation | 25° C. - 30 days | 40° C. - 30 days |
|---|---|---|---|
| Residual ratio of KW-3902 | 100% | 101% | 102% |
| Discoloration | 0.001 | 0.000 | 0.001 |
| Average particle diameter | 0.12 μm | 0.11 μm | 0.11 μm |

What is claimed is:

1. An oil-in-water emulsion containing a xanthine derivative represented by formula (I)

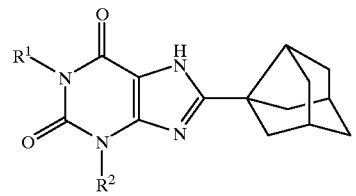

(I)

wherein $R^1$ and $R^2$ independently represent a substituted or unsubstituted lower alkyl group, and Q represents hydrogen, a hydroxyl group or a hydroxyl group derivative, or its pharmacologically acceptable salt, and wherein said xanthine derivative or salt is present within an oil phase of said emulsion.

2. The oil-in-water emulsion according to claim 1, further comprising a surfactant, and a pharmaceutically acceptable carrier.

3. The oil-in-water emulsion as in claim 1 or 2, wherein the xanthine derivative is 8-(3-noradamantyl)-1,3-dipropylxanthine.

4. The oil-in-water emulsion as in claim 1, wherein the oil is contained in an amount from 0.5% to 30% (w/v).

5. The oil-in-water emulsion as in claim 4, wherein the xanthine derivative is 8-(3-noradamantyl)-1,3-dipropylxanthine.

6. The oil-in-water emulsion as in claim 1 or 2, wherein the oil is soybean oil.

7. The oil-in-water emulsion as in claim 1, wherein the xanthine derivative is 8-(3-noradamantyl)-1,3-dipropylxanthine and the oil is soybean oil.

8. The oil-in-water emulsion as in claim 1, wherein said oil being contained in an amount from 0.5% to 30% (w/v) and the oil is soybean oil.

9. The oil-in-water emulsion, as in claim 8, wherein the xanthine derivative is 8-(3 noradamantyl)-1,3-dipropylxanthine.

10. The oil-in-water emulsion as in claim 1 or 2, having a particle diameter between 0.02 and 0.15 μm.

11. The oil-in-water emulsion as in claim 10, wherein the xanthine derivative is 8-(3- noradamantyl)-1,3-dipropylxanthine.

12. The oil-in-water emulsion as in claim 1, having a particle diameter between 0.02 and 0.15 μm, the oil being contained in an amount from 0.5% to 30% (w/v).

13. The oil-in-water emulsion as in claim 1, having a particle diameter between 0.02 and 0.15 μm, wherein the oil is soybean oil.

14. The oil-in-water emulsion as in claim 13, wherein the xanthine derivative is 8-(3-noradamantyl)-1,3-dipropylxanthine.

15. The oil-in-water emulsion as in claim 1, having a particle diameter between 0.02 and 0.15 µm, wherein the xanthine derivative is 8-(3-noradamantyl)-1,3-dipropylxanthine, said oil being contained in an amount from 0.5% to 30% (w/v).

16. The oil-in-water emulsion as in claim 1, having a particle diameter between 0.02 and 0.15 µm, wherein the oil is soybean oil, the oil being contained in an amount from 0.5% to 30% (w/v).

17. The oil-in-water emulsion as in claim 16, wherein the xanthine derivative is 8-(3-noradamantyl)-1,3-dipropylxanthine.

18. The oil-in-water emulsion as in claim 1 or 2, wherein the emulsion is a freeze-dried preparation.

19. The oil-in-water emulsion as in claim 18, wherein the xanthine derivative is 8-(3-noradamantyl)-1,3-dipropylxanthine.

20. The oil-in-water emulsion as in claim 1, wherein the emulsion is a freeze-dried preparation, and said oil is contained in an amount from 0.5% to 30% (w/v).

21. The oil-in-water emulsion as in claim 1, wherein the emulsion is a freeze-dried preparation and the oil is soybean oil.

22. The oil-in-water emulsion as in claim 1 or 2, having a particle diameter between 0.02 and 0.15 µm, and wherein the emulsion is a freeze-dried preparation.

23. The oil-in-water emulsion as in claim 1, wherein the emulsion is a freeze-dried preparation, and the xanthine derivative is 8-(3 noradamantyl)-1,3-dipropylxanthine, the oil being contained in an amount from 0.5% to 30% (w/v).

24. The oil-in-water oil emulsion as in claim 1, wherein the emulsion is a freeze-dried preparation, the xanthine derivative is 8-(3-noradamantyl)-1, 3-dipropylxanthine, and the oil is soybean oil.

25. The oil-in-water emulsion as in claim 1 or 2, having a particle diameter between 0.02 and 0.15 µm, wherein the emulsion is a freeze-dried preparation and the xanthine derivative is 8-(3-noradamantyl)-1,3-dipropylxanthine.

26. The oil-in-water emulsion as in claim 1, wherein the emulsion is a freeze-dried preparation, the oil is soybean oil and is contained in an amount from 0.5% to 30% (w/v).

27. The oil-in-water emulsion as in claim 1, having a particle diameter between 0.02 and 0.15 µm, wherein the emulsion is a freeze-dried preparation, the oil being contained in an amount from 0.5% to 30% (w/v).

28. The oil-in-water emulsion as in claim 1, having a particle diameter between 0.02 and 0.15 µm, wherein the emulsion is a freeze-dried preparation, and the oil is soybean oil.

29. The oil-in-water emulsion as claimed in claim 1, wherein the emulsion is a freeze-dried preparation, the xanthine derivative is 8-(3 noradamantyl)-1,3-dipropylxanthine, and the oil is soybean oil contained in an amount from 0.5% to 30% (w/v).

30. The oil-in-water emulsion as claimed in claim 1, having a particle diameter between 0.02 and 0.15 µm, wherein the emulsion is a freeze-dried preparation, the xanthine derivative is 8-(3 noradamantyl)-1,3-dipropylxanthine, and the oil is soybean oil.

31. The oil-in-water emulsion as in claim 1, having a particle diameter between 0.02 and 0–15 µm wherein the emulsion is a freeze-dried preparation, and the oil is soybean oil contained in an amount from 0.5% to 30% (w/v).

32. The oil-in-water emulsion as in claim 31, wherein the xanthine derivative is 8-(3-noradamantyl)-1,3-dipropylxanthine.

33. The oil-in-water emulsion as in claim 2, wherein the surfactant is a phospholipid.

34. The oil-in-water emulsion as in claim 33, wherein the oil is contained in an amount from 0.5% to 30% (w/v), and the surfactant is contained in an amount from 0.1 to 2 times by weight based on said oil.

35. The oil-in-water emulsion as in claim 34, wherein the xanthine derivative is 8-(3-noradamantyl)-1,3-dipropylxanthine.

36. The oil-in-water emulsion as in claim 35, having a particle diameter between 0.02 and 0.15 µm, wherein the oil is soybean oil, and the surfactant is phosphatidyl choline.

37. The oil-in-water emulsion as in claim 2, wherein the oil is contained in an amount from 0.5% to 30% (w/v) and surfactant is contained in an amount from 0.1 to 2 times by weight based on said oil.

38. The oil-in-water emulsion as in claim 37, wherein the xanthine derivative is 8-(3-noradamantyl)-1,3-dipropylxanthine.

39. The oil-in-water emulsion as in claim 2, wherein the oil is soybean oil, and the surfactant is phosphatidyl choline.

40. The oil-in-water emulsion as in claim 2, wherein the xanthine derivative is 8-(3-noradamantyl)-1,3-dipropylxanthine, the oil is soybean oil, and the surfactant is phosphatidyl choline.

41. The oil-in-water emulsion as in claim 2, said oil being contained in an amount from 0.5% to 30% (w/v), said surfactant being contained in an amount from 0.1 to 2 times by weight based on said oil, the oil is soybean oil, and the surfactant is phosphatidyl choline.

42. The oil-in-water emulsion, as in claim 41, wherein the xanthine derivative is 8-(3 noradamantyl)-1,3-dipropylxanthine.

43. The oil-in-water emulsion as in claim 2, having a particle diameter between 0.02 and 0.15 µm, the oil being contained in an amount from 0.5% to 30% (w/v) and said surfactant being contained in an amount from 0.1 to 2 times by weight based on said oil.

44. The oil-in-water emulsion as in claim 2, having a particle diameter between 0.02 and 0.15 µm, wherein the oil is soybean oil, and the surfactant is phosphatidyl choline.

45. The oil-in-water emulsion as in claim 44, wherein the xanthine derivative is 8-(3-noradamantyl)-1,3-dipropylxanthine.

46. The oil-in-water emulsion as in claim 2, having a particle diameter between 0.02 and 0.15 µm, wherein the xanthine derivative is 8-(3-noradamantyl)-1,3-dipropylxanthine, said oil being contained in an amount from 0.5% to 30% (w/v), and said surfactant being contained in an amount from 0.1 to 2 times by weight based on said oil.

47. The oil-in-water emulsion as in claim 2, having a particle diameter between 0.02 and 0.15 µm, wherein the oil is soybean oil, and the surfactant is phosphatidyl choline, the oil being contained in an amount from 0.5% to 30% (w/v) and the surfactant being contained in an amount from 0.1 to 2 times by weight based on said oil.

48. The oil-in-water emulsion as in claim 47, wherein the xanthine derivative is 8-(3-noradamantyl)-1,3-dipropylxanthine.

49. The oil-in-water emulsion as in claim 2, wherein the emulsion is a freeze-dried preparation, said oil being contained in an amount from 0.5% to 30% (w/v) and the surfactant being contained in an amount from 0.1 to 2 times by weight based on said oil.

50. The oil-in-water emulsion as in claim 2, wherein the emulsion is a freeze-dried preparation, the oil is soybean oil, and the surfactant is phosphatidyl choline.

51. The oil-in-water emulsion as in claim 2, wherein the emulsion is a freeze-dried preparation, and the xanthine derivative is 8-(3 noradamantyl)-1,3-dipropylxanthine, the oil being contained in an amount from 0.5% to 30% (w/v) and the surfactant being contained in an amount from 0.1 to 2 times by weight based on said oil.

52. The oil-in-water oil emulsion as in claim 2, wherein the emulsion is a freeze-dried preparation, the xanthine derivative is 8-(3-noradamantyl)-1,3-dipropylxanthine, the oil is soybean oil, and the surfactant is phosphatidyl choline.

53. The oil-in-water emulsion as in claim 2, wherein the emulsion is a freeze-dried preparation, the oil is soybean oil, the surfactant is phosphatidyl choline, the oil being contained in an amount from 0.5% to 30% (w/v), and the surfactant being contained in an amount from 0.1 to 2 times by weight based on said oil.

54. The oil-in-water emulsion as in claim 2, having a particle diameter between 0.02 and 0.15 $\mu$m, wherein the emulsion is a freeze-dried preparation, the oil being contained in an amount from 0.5% to 30% (w/v), and the surfactant being contained in an amount from 0.1 to 2 times by weight based on said oil.

55. The oil-in-water emulsion as in claim 2, having a particle diameter between 0.02 and 0.15 $\mu$m, wherein the emulsion is a freeze-dried preparation, the oil is soybean oil, and the surfactant is phosphatidyl choline.

56. The oil-in-water emulsion as claimed in claim 2, wherein the emulsion is a freeze-dried preparation, the xanthine derivative is 8-(3 noradamantyl)-1,3-dipropylxanthine, the oil is soybean oil, and the surfactant is phosphatidyl choline, the oil being contained in an amount from 0.5% to 30% (w/v), the surfactant is contained in an amount from 0.1 to 2 times by weight based on said oil.

57. The oil-in-water emulsion as claimed in claim 2, having a particle diameter between 0.02 and 0.15 $\mu$m, wherein the emulsion is a freeze-dried preparation, the xanthine derivative is 8-(3 noradamantyl)-1,3-dipropylxanthine, the oil is soybean oil, and the surfactant is phosphatidyl choline.

58. The oil-in-water emulsion as in claim 2, having a particle diameter between 0.02 and 0–15 $\mu$m wherein the emulsion is a freeze-dried preparation, the oil is soybean oil, and the surfactant is phosphatidyl choline, the oil being contained in an amount from 0.5% to 30% (w/v), and the surfactant being contained in an amount from 0.1 to 2 times by weight based on said oil.

59. The oil-in-water emulsion as in claim 58, wherein the xanthine derivative is 8-(3-noradamantyl)-1,3-dipropylxanthine.

\* \* \* \* \*

UNITED STATES PATENT AND TRADEMARK OFFICE
CERTIFICATE OF CORRECTION

PATENT NO. : 6,210,687 B1   Page 1 of 1
DATED : April 3, 2001
INVENTOR(S) : Toshihito Hosokawa et al.

It is certified that error appears in the above-identified patent and that said Letters Patent is hereby corrected as shown below:

Column 1,
Line 50, "emulsions" should read -- emulsion --.

Column 8,
Line 12, "and" should read -- and the --.

Signed and Sealed this

Thirtieth Day of April, 2002

Attest:

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.    : 6,210,687 B1
DATED         : April 3, 2001
INVENTOR(S)   : Toshihito Hosokawa et al.

It is certified that error appears in the above-identified patent and that said Letters Patent is hereby corrected as shown below:

Title page,
Item [57], ABSTRACT,
Lines 17-26, please amend the formula to read as follows:

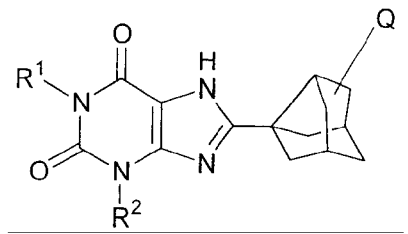

Signed and Sealed this

Sixteenth Day of March, 2004

JON W. DUDAS
*Acting Director of the United States Patent and Trademark Office*